(12) United States Patent
Rao et al.

(10) Patent No.: US 7,071,341 B2
(45) Date of Patent: *Jul. 4, 2006

(54) α-GLUCOSIDASE INHIBITORS AND THEIR SYNTHESIS FROM A NATURAL SOURCE

(75) Inventors: Janaswamy Madhusudana Rao, Hyderabad (IN); Rao Jagadeeshwar Rao, Hyderabad (IN); Upparapalli Sampath Kumar, Hyderabad (IN); Singireddy Venkat Reddy, Hyderabad (IN); Ashok Kumar Tiwari, Hyderabad (IN); Jhillusingh Yadav, Hyderabad (IN); Kondapuram Vijaya Raghavan, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 11 days.

This patent is subject to a terminal disclaimer.

(21) Appl. No.: 10/403,034

(22) Filed: Apr. 1, 2003

(65) Prior Publication Data
US 2004/0171674 A1    Sep. 2, 2004

Related U.S. Application Data

(63) Continuation-in-part of application No. 10/375,033, filed on Feb. 28, 2003.

(51) Int. Cl.
C07D 311/74 (2006.01)
(52) U.S. Cl. .................. 549/399
(58) Field of Classification Search .......... 549/399; 514/456
See application file for complete search history.

(56) References Cited

OTHER PUBLICATIONS

Collins, FM 'Current treatment approaches to type 2 diabetes mellitus: success and shortcomings' PMID: 12408409 (2002).*
Scheen, AJ 'Treatment of diabetes in patients with severe obesity' Biomed & Pharmacother (2000) 54:74-79.*

* cited by examiner

Primary Examiner—Amelia A. Owens
(74) Attorney, Agent, or Firm—Sughrue Mion, PLLC

(57) ABSTRACT

The present invention provides novel α-glucosidase inhibitory compound (−)-mesquitol and its analogs isolated in significant yield from traditional medicinal plant *Dichrostachys cinerea* and further modification of (−)-mesquitol to enhance the α-glucosidase inhibitory potential; the invention also identifies the usage of (−)-mesquitol and its analogues, based on their α-glucosidase inhibitory activity, as broad based potential therapeutics as antihyperglycernic, antidiabatic, antiobesity, antiviral, anticancer, immunestimulants and the like.

14 Claims, 1 Drawing Sheet

1

Scheme-1

Figure 1:
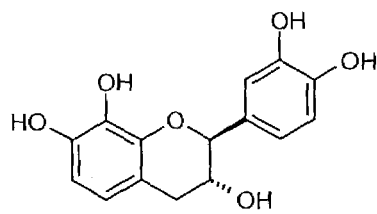
Figure 1:
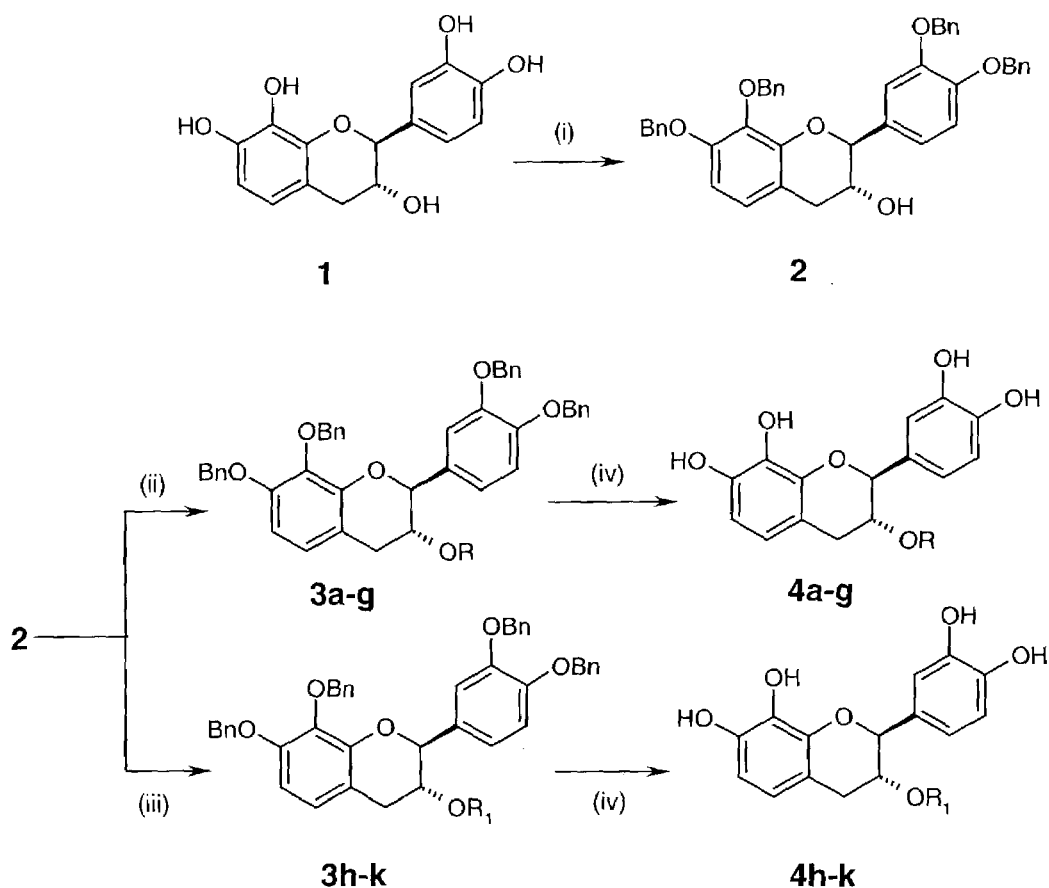

Reagents and conditions:
(i) Benzyl bromide, K₂CO₃, acetone, reflux 5h
(ii) Corresponding aliphatic acid, Dicyclohexylcarbodiimide, 4-N,N'-dimethylaminopyridine, methylene chloride
(iii) Corresponding aromatic acid chloride, triethyl amine, methylene chloride
(iv) H₂, 10%Palladium on carbon, methanol.

1

Scheme-1

Reagents and conditions:

(i) Benzyl bromide, K₂CO₃, acetone, reflux 5h
(ii) Corresponding aliphatic acid, Dicyclohexylcarbodiimide, 4-N,N'-dimethylaminopyridine, methylene chloride
(iii) Corresponding aromatic acid chloride, triethyl amine, methylene chloride
(iv) H₂, 10%Palladium on carbon, methanol.

though by pharmaceutical
α-GLUCOSIDASE INHIBITORS AND THEIR SYNTHESIS FROM A NATURAL SOURCE (This is a CIP Application of U.S. application Ser. No. 10/375,033 filed on Feb. 28, 2003).

FIELD OF INVENTION

This invention relates to the identification of novel α-glucosidase inhibitory compound (−)-mesquitol isolated in significant yield from traditional medicinal plant *Dichrostachys cinerea* and further modification of (−)-mesquitol to enhance the α-glucosidase inhibitory potential. This invention also identifies the usage of (−)-mesquitol and its analogues, based on their α-glucosidase inhibitory activity, as broad based potential therapeutics as antihyperglycemic, antidiabetic, antiobesity, antiviral, anticancer, immunestimulants and the like.

BACKGROUND OF THE INVENTION

It is described that an α-glucosidase inhibitors inhibits the α-glucosidase localized at the fine villies in the small intestine, and controls the rapid increase in blood glucose after meal and next increase in blood insulin level (*Diabetes Medicine*, 10, 688, 1993). Since they suppresses/slow down the metabolism of dietary carbohydrates in human and animals, and exhibit an inhibitory effect of blood glucose increases, they are found effective in improving hyperglycemic conditions as well as various diseases induced by hyperglycemia such as obesity and diabetes.

Glucosidases are also found involved in the transformation of normal cells to cancer cells and in tumor cell invasion and migration. It has also been observed that level of serum glucosidases are elevated in many patients with different tumors and are thought to be involved in the degradation of the extra cellular matrix in tumor cell invasion (*Cancer Matastasis Rev.* 4, 81, 1985). Therefore, the use of glucosidase inhibitors to prevent abberations during glycoprotein processing and to inhibit catabolic glycosidases is being actively pursued as therapeutic strategy for cancer. (*Phytochemistry* 56, 265, 2001).

Furthermore, many animal viruses contain an outer envelop, which is composed of one or more viral glycoprotein. These glycoproteins are often essential proteins in that they are required in the viral life cycle, either in viron assembly and secretion and/or infectivity. As the processing of these glycoproteins occurs through the cellular machinery, inhibitors of processing α-glucosidases have been shown to decrease the infectivity of broad range of human pathogenic viruses (*FEBS letters* 430, 17, 1998 and *Phytochemistry* 56, 265, 2001).

Similarly, α-glucosidase inhibitors have also been found to restore the immune response of immunocompromized experimental animals (*Chem. Pharm. Bull*. 39, 2807, 1991). Therefore α-glucosidase inhibitors are also extensively been worked out for their exploitation as immunostimulants.

There are several α-glucosidase inhibitors known in the literature and are under clinical practice (*Phytochemistry* 56, 265, 2001). However, it is still felt that when more of the α-glucosidase inhibitor compounds of natural origin with varied skeleton become available commercially, there is sure to be even wider range of potentially valuable activities found than shown to date.

Plants continue to be used world wide for the treatment of disease and novel drug entities continue to be developed through research in to their constituents. Despite the massive arsenal of clinical agents developed by the pharmaceutical industry there has been aversion by many members of the public. This public aversion further paved the way for use of herbal medicines. Therefore, herbal remedies have proved to be popular as alternative treatment of disease. Due to this powerful Green Wave sweeping all over the world, the demand for herbal drug has increased several folds.

This current trend has accelerated the scientific investigations and evaluation of folklore and traditional medicinal plants used for the treatment of variety of ailments world over. These efforts have led to the isolation and identification of several novel chemical entities. These chemical entities were also found to possess variety of biological activities of multiple therapeutic importances.

*Dichrostachys cinerea* is a medicinal plant used in the traditional Indian system of medicine. It is widely advocated in diuretic, lithotriptic, anodyne, and inflammatory conditions. Further, it is found useful in arthralgia, elephantiasis, dyspepsia, diarrhea, nephropathy etc (*Indian Medicinal Plants*, Vol. 2 p. 330, 1995). *Dichrostachys cinerea* is also found useful in opthalmia, rheumatism, urinary calculi and renal troubles (*Wealth of India* Vol. 3 p. 56, 1952) and has been reported to possess protease inhibitory (CA, 90, 118086u), antifungal (*Ind. J. Plant. Physiol*, 29, 278–80, 1986), and antibacterial activity (*Fitoterapia*, 59, 57–62, 1988.).

In this invention, (−)-mesquitol is isolated from the methanolic extract of stem of *Dichrostachys cinerea* in very good yield (1.5% yield from the dried plant material). (−)-mesquitol is an optical isomer of (+)-mesquitol which was previously isolated from *Prosopis grandulosa* in 0.01% yield (*J. Chem. Soc. Perkin. Trans I*, 1737, 1986). However, this isomer of mesquitol has not been tested for any biological activity to the best of our search.

Despite the wide use of *Dichrostachys cinerea* in Indian traditional system of medicinal practice, efforts of isolating and identifying biologically active molecules are still lacking. As molecules isolated from traditional medicinal plants have shown multiple biological activities of therapeutic importance, we investigated *Dichrostachys cinerea* and observed that (−)-mesquitol is present in *D. cinerea* in significant yield and possess potent α-glucosidase inhibitory activity, which may find broad therapeutic application. We also made efforts to prepare analogues of the compound (−)-mesquitol in order to enhance the α-glucosidase inhibitory activity.

OBJECTS OF THE INVENTION

The main object of the present invention is to provide (−)-mesquitol and analogues of (−)-meaquitol.

Another object of the invention is to provide semi-synthetic 3-O-alkyl or aryl esters of (−)-mesquitol.

Still another object of the invention is to provide pharmaceutical compositions comprising (−)-mesquitol or its semi-synthetic 3-O-alkyl or aryl esters to provide α-glucosidase inhibitor.

Still another object of the invention is t provide a process for the isolation of (−)-mesquitol from *Dichrostachys cinerea*.

Furthermore, the object of the invention relates to enhance the α-glucosidase inhibitory potential of the parent compound (−)-mesquitol by preparing the esters, which includes both aliphatic and aromatic.

SUMMARY OF THE INVENTION

Accordingly, the present invention provides novel α-glucosidase inhibitory compound (−)-mesquitol and its analogs isolated in significant yield from traditional medicinal plant *Dichrostachys cinerea* and further modification of (−)-mesquitol to enhance the α-glucosidase inhibitory potential. This invention also identifies the usage of (−)-mesquitol and its analogues, based on their α-glucosidase inhibitory activity, as broad based potential therapeutics as antihyperglycemic, antidiabatic, antiobesity, antiviral, anticancer, immunestimulants and the like

DETAILED DESCRIPTION OF THE INVENTION

Accordingly, the present invention provides (−)-Mesquitol and its semi-synthetic 3-O-alkyl or aryl esters represented by the general formula (4)

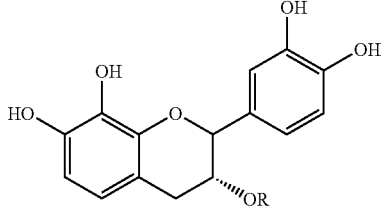

FORMULA (4)

wherein, R=H, $C_nH_{2n+1}$ (n=1 to 16); —$COC_6H_4X$ [wherein X=H, F, Cl, Br, I, $NO_2$, CN, $NH_2$, $OR_1$ {$R_1$=H; $C_nH_{2n+1}$ (n=1 to 8)}]

In an embodiment of the present invention, the preferred compounds of general formula

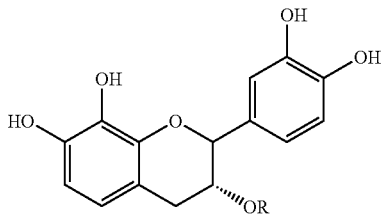

(4), where R selected is listed in the following table:

| Serial No. | Compound Code | R |
|---|---|---|
| 1. | 4a | Acetyl |
| 2. | 4b | Butyryl |
| 3. | 4c. | Hexanoyl |
| 4. | 4d. | Decanoyl |
| 5. | 4e | Myristoyl |
| 6. | 4f | Palmitoyl |
| 7. | 4g | Stearoyl |
| 8. | 4h | Benzoyl |
| 9. | 4i | o-chloro benzoyl |
| 10. | 4j | p-methoxy benzoyl |
| 11. | 4k | p-flouro benzoyl |

An embodiment of the invention, the said compounds exhibit α-glucosidase inhibitory activity.

In another embodiment, the α-glucosidase inhibitory activity of 3-O-aliphatic esters of (−) mesquitol increases with an increase in carbon chain length up to sixteen carbon atoms.

Still another embodiment, palmitoyl, myristoyl and decanoyl esters of (−) mesquitol are more potent α-glucosidase inhibitors than the standard drug 1-deoxy nojirimycin.

Still another embodiment, the α-glucosidase inhibitors of 3-O-aromatic esters of (−) mesquitol are better than the parent compound.

Yet another embodiment, the benzoyl and p-flourobenzyl ester of (−) mesquitol are more potent α-glucosidase inhibitor than the standard drug 1-deoxy nojirimycin.

Still yet another embodiment, the above said compound (−) mesquitol and its analogues are useful in the management and treatment of diseases like hyperglycenua, hyper insulinemia, hypolipoproteinemia, cancer, viral infection, hepatitis B and C, HIV and AIDS.

The $IC_{50}$ values of the compounds are in the range of 32.0 to 83.0 μm.

One more embodiment of the invention provides a pharmaceutical composition for α-glucosidase inhibitor activity, the said composition comprising administering a pharmaceutically effective dosage of (−) mesquitol or its analogues or combination thereof to the subject in need of.

Another embodiment of the invention, the composition optionally comprises pharmaceutically acceptable additives. The additive is selected from nutrients such as proteins, carbohydrates, sugars, talc, magnesium stearate, cellulose, calcium carbonate, starch-gelatin paste and/or pharmaceutically acceptable carriers, excipient, diluents or solvent.

Another embodiment of the invention, the above composition is used singly or in combination with pharmaceutically acceptable analogues.

Still another embodiment of the invention, the said composition may comprise pharmaceutically acceptable additives such as carrier, diluents, and adjuvant.

Still another embodiment, the composition may be administered systemically or orally.

Yet another embodiment, the subject are selected from animals or mammals, preferably humans.

One more embodiment of the invention provides a process for the preparation of semisynthetic 3-O-alkyl or aryl esters of (−) mesquitol, the said process comprising steps of:

a) drying the wood of Dichrostachys cinerea in shade,
b) powdering the shade dried wood of step (a),
c) extracting the powder of step (b) with petroleum ether, followed by halogenated hydrocarbon solvent to obtain the plant extracts and a plant residue,
d) soaking the plant residue of step (c) in methanol, filtering and concentrating the methanol extract to obtain a residue,
e) purifying the residue of step (d) over silica gel column by eluting with mixture of organic solvent,
f) obtaining pure (−) mesquitol,
g) adding to (−) mesquitol of step (f) anhydrous potassium carbonate, a ketonic solvent, benzyl halide and refluxed the mixture under nitrogen atmosphere for a time period of 2 hour to 8 hour,
h) filtering the mixture of step (g), washing the residue with ketonic solvent, combining the filtrate and the wash, evaporating under reduced pressure to obtain a residue,
i) purifying the residue of step (h) to obtain pure terra-O-benzyl-mesquitol of formula (2), j) treating the compound of formula (2) of step (i) with N,N'-Dicyclohexyl carbodiimide (DCC) required aliphatic acid in an anhydrous methylene chloride under nitrogen atmosphere followed by addition of 4-dimethyl aminopyridine, stirring the mixture for 6 h to 18 h at room temperature, filtering the mixture, washing the residue with methylene chloride, combining the filtrate and washing to obtain methylene chloride solution, k) washing the methylene chloride solution of step (j) with water, drying over anhydrous sodium sulphate, filtered, evaporating the solvent to obtain a residue, l) purifying the residue of step (k) to obtain the required 3-O-alkyl esters of tetra-o-benzyl (−) mesquitol of formulae 3a to 3g.

m) providing a cooled solution of compound (2) in anhydrous methylene chloride along with triethyl amine, flushing nitrogen, n) adding required benzoyl chloride to step (m) mixture stirring the mixture for 2 h to 6 h at an ambient temperature, o) adding water to the reaction mixture of step (n), extracting with methylene chloride, separating methylee chloride layer and aqueous layer, p) drying methylene chloride layer of step (o) over anhydrous sodium sulphate, filtering and evaporating the solvent to obtain a residue, q) purifying the residue of step (p) to obtain 3-O-aryl ester of tetra-o-benzyl (−) mesquitol of formula 3h to 3k, and r) stirring the compound of step (l) or step (q) in an alcoholic solution in the presence of palladium charcoal and hydrogen for a time period of 4 h to 8 h at room temperature, and s) filtering the mixture of step (r), removing the solvent from the filtrate to obtain the required 3-O-alkyl or aryl esters of (−) mesquitol of general formula (4).

Another embodiment of the invention, the mixture of organic solvent used for eluting, is a mixture of chloroform and methanol, wherein the mixture of solvent used is chloroform-methanol (96:4).

Another embodiment, the ketonic solvent used is selected from ethyl-methyl ketone, acetone and methyl isobutyl ketone, preferably acetone.

Still another embodiment, the aliphatic acid used is selected from a group consisting of acetic acid, butyric acid, hexanoic acid, decanoic acid, myristic acid, palmitic acid or stearic acid.

Yet another embodiment, the benzoyl chloride used is selected from a group consisting of halo benzoyl chloride, alkoxy benzoyl chloride, cyano benzoyl chloride, amino benzoyl chloride and nitro benzoyl chloride.

Yet another embodiment, the halo benzoyl chloride used is o-chlorobenzoyl chloride or p-fluoro benzoyl chloride.

Yet another embodiment, the alkoxy benzoyl chloride used is p-methoxy benzyl chloride.

Another embodiment, the 3-O-esters of (−) mesquitol obtained exhibit α-inhibitor activity.

Yet another embodiment, the α-glucosidase inhibitory activity of 3-O-aliphatic esters of (−) mesquitol increases with an increase in carbon chain length upto sixteen carbon atoms.

Yet another embodiment, palmitoyl, myristoyl and decanoyl esters of (−) mesquitol are more potent than the standard α-glucosidase inhibitor 1-deoxy nojirimycin.

Yet another embodiment, the α-glucosidase inhibition of 3-O-aromatic esters of (−) mesquitol is better than the parent compound.

Yet another embodiment, the 3-O aromatic esters of (−) mesquitol are benzoyl, o-chlorobenzoyl, p-methoxy benzoyl or p-fluoro benzoyl esters.

Yet another embodiment, the benzoyl and p-flourobenzyl ester of (−) mesquitol are more potent than the standard α-glucosidase inhibitor 1-deoxy nojirimycin.

Yet another embodiment, the 3-O-alkyl or aryl esters of (−) mesquitol obtained are useful in the management and treatment of diseases like hyperglycemia, hyper insulinemia, hypolipoproteinemia, cancer, viral infection, hepatitis B and C, HIV and AIDS.

Yet another embodiment, the 3-O-alkyl or aryl esters of (−) mesquitol obtained has $IC_{50}$ value in the range of 32.0 to 83.0 μm.

In the present invention, a compound selected from the group consisting of semi-synthetic occurring compounds represented by the general formula 4, which includes aliphatic and aromatic esters of (−)-mesquitol (Scheme-1) and their usage as α-glucosidase inhibitors. Where R is selected from a group consisting of acetyl, butyryl, hexanoyl, decanoyl, myrystoyl, palmitoyl and steroyl in the case of aliphatic esters. Where $R_1$ is selected from the group consisting of benzoyl, p-methoxy benzoyl, o-chloro benzoyl and p-flouro benzoyl in the case of aromatic esters.

The aliphatic esters of (−)-mesquitol (4a–g) are prepared by the condensation of (−)-3',4',7,8-tetra-O-benzyl mesquitol with the corresponding aliphatic acid in the presence of Dicyclohexyl carbodiimide followed by debenzylation. The aromatic esters of (−)-mesquitol (4h–k) are prepared by the reaction of (−)-3',4',7,8-tetra-O-benzyl mesquitol with corresponding acid chloride in the presence of triethylamine followed by debenzylation. The synthetic routes yielded the required target compounds in moderate to good yields.

The application also relates to the pharmaceutical compositions comprising an effective amount of compound according to formula 4a–g or 4h–k together with a pharmaceutically acceptable carrier and to methods as α-glucosidase inhibitors in management and treatment of human diseases like hyperglycemia, hyperinsulinemia, hyperlipoproteinemea, cancer, viral infection, hepatitis B and C, HIV and AIDS etc.

The present invention embodies α-glucosidase inhibitory activities to the aliphatic esters and aromatic esters of (−)-mesquitol. The α-glucosidase inhibitory potential of aliphatic esters has shown steady increase with the increase in the chain length up to a length of sixteen carbons. All the aromatic esters have shown better α-glucosidase inhibitory potential than the parent compound, (−)-mesquitol.

A method for synthesizing non-naturally occurring esters of (−)-mesquitol which includes aliphatic and aromatic. All the compounds are useful as potential α-glucosidase inhibitors. α-glucosidase inhibitors present a broad spectrum of biological activities useful for therapeutic applications as antihyperglycemic, antiviral, anti-HIV, and anti cancer and so on. The aliphatic esters are prepared by the condensation of (−)-3',4',7,8-tetra-O-benzyl mesquitol with the corresponding aliphatic acid in the presence of Dicyclohexyl carbodiimide followed by debenzylation. The aromatic esters are prepared by the reaction of (−)-3',4',7,8-tetra-O-benzyl mesquitol with corresponding acid chloride in the presence of triethylamine followed by debenzylation. The synthetic schemes yielded the required target compounds in moderate to good yields. Both the aliphatic esters and aromatic esters were tested for their α-glucosidase (yeast) inhibitory potential. The aliphatic esters have shown steady increase in their inhibitory activity with the corresponding increase in the chain length up to a length of sixteen carbons followed by decrease in the activity. All the aromatic esters showed better α-glucosidase inhibitory activity than the parent compound (−)-mesquitol.

The following examples are provided as illustration only and should not be construed to limit the scope of the present invention. Any average person skilled in the art can able to perform the invention.

EXAMPLES

Example 1

A. Isolation of (−)-mesquitol (1)

The shade dried wood powder of *D. cinerea* (2 Kg) was loaded on a soxhlet apparatus, extracted with petroleum ether followed by extraction with chloroform. The residue obtained after extraction with petroleum ether and chloroform was soaked in methanol for 24 hr at room temperature. The methanol extract was filtered and concentrated under vacuum to obtain 50 g of the extract. The extract was then subjected to column chromatography using silica gel (60–120 mesh). The column is eluted with chloroform methanol gradient. The fractions eluted at 4% methanol in chloroform yielded (−)-mesquitol (30 g).

Example 2

B. Preparation of (−)-3',4',7,8-tetra-O-benzyl mesquitol (2)

To a mixture of (−)-mesquiteol 1 (1 g, 3.45 mmol), anhydrous potassium carbonate (2.41 g, 17.2 mmol) in 20 ml acetone, benzyl bromide (2.96 g, 17.2 mmol) was added. The mixture was refluxed under nitrogen atmosphere for 4 h. After completion of the reaction potassium carbonate was filtered washed with excess of acetone (2×50 ml). The combined acetone layers are concentrated under vacuum. The residue was purified by column chromatography on silica gel (60–120 mesh) to yield (−)-3',4',7,8-tetra-O-benzyl mesquitol 2 (2 g) in pure form.

Example 3

C. Preparation of 3-O-aliphatic esters of (−)-3',4',7, 8-tetra-O-benzyl mesquitol (3a–g)

The aliphatic esters (Scheme. 1) were prepared by condensing the corresponding acids with (−)-3',4',7,8-tetra-O-benzyl mesquitol 2 in the presence of N,N'-Dicyclohexyl carbodiimide (DCC). In brief the corresponding acid (0.308 mmol) and DCC (0.370 mmol) were cooled and stirred in anhydrous methylene chloride (5 ml) for 15 min under nitrogen atmosphere. To this mixture compound 2 (0.308 mmol) in anhydrous methylene chloride (3 ml) was added followed by the addition of catalytic amount of 4-Dimethylamino pyridine (0.030 mmol). The entire mixture was stirred at room temperature for 12 hr under nitrogen. After completion of the reaction, the reaction mixture was filtered and washed with methylene chloride (2×10 ml). The combined organic layers were washed with water (2×25 ml), dried over anhydrous sodium sulphate and concentrated under vacuum. The residue was purified by chromatography on silica gel (60–120 mesh) to give the corresponding 3-O-esters of (−)-3',4',7,8-tetra-O-benzyl mesquitol 2 (3a–g) in excellent yields.

Example 4

D. Preparation of 3-O-aromatic esters of (−)-3',4',7, 8-tetra-O-benzyl mesquitol (3h–k)

(Scheme. 1) The (−)-3',4',7,8-tetra-O-benzyl mesquitol 2 (0.308 mmol) was cooled in anhydrous methylene chloride (5 ml) along with triethylamine (0.370 mmol) under nitrogen atmosphere. To this mixture the acid chloride (0.370 mmol) of the corresponding aromatic acid was added and stirred for 4 hr. After completion of the reaction, the reaction mixture was diluted with water, extracted with methylene chloride (2×10 ml), dried over anhydrous sodium sulphate and concentrated under vacuum. The residue was purified by column chromatography on silica gel (60-120 mesh) to yield the corresponding 3-O-esters of (−)-3',4',7,8-tetra-O-benzyl mesquitol 2 (3h–k) in excellent yields.

Example 5

E. Preparation of 3-O-aliphatic and Aromatic Esters of (−)-mesquitol (4a–k)

Both the aliphatic and aromatic esters of 3',4',7,8-tetra-O-benzyl mesquitol (3a–g and 3h–k) were hydrogenolysed using palladium on carbon under hydrogen atmosphere. In general to a solution of the ester in methanol, palladium on carbon (10 mol %) was added and the mixture was stirred under hydrogen balloon for 5 h at room temperature. The catalyst was filtered over celite washed with methanol and the methanolic solution was concentrated under reduced pressure to obtain 3-O-aliphatic and aromatic esters of (−)-mesquitol (4a–k).

Example 6

F. Determination of α-Glucosidase Inhibition Activity of Compounds

The α-glucosidase inhibitory assay was done by the chromogenic method. In brief 10 μl of test compounds dissolved in DMSO (5 mg/ml and subsequent dilutions) were incubated for 5 min. with 50 μl of yeast α-glucosidase [Sigma] enzyme prepared in 100 mM phosphate buffer (pH 7.00). After 5 minutes of incubation, 50 μl of 5 mM substrate (p-nitrophenyl-α-D-glucopyranoside [Sigma] prepared in the same buffer) was added. The pre-substrate and 5-min post-substrate addition absorbances were recorded at 405 nm spectrophotometrically. The increase in absorbance from pre-substrates addition to post substrates reaction were obtained. Percent inhibition was calculated by (1-Absorbance test/Absorbance control)×100 and 50% inhibitory concentration (IC50) was calculated by applying suitable regression analysis.

The physical and spectral data of the compounds:

1. (−)-mesquitol (1): m.p 252° C., EIMS 290 ($M^+$), $^1$H NMR (200 MHz, acetone-$d_6$) δ 7.95 (2-OH, s), 7.25, 7.55 (2-OH, each singlet), 6.88–6.72 (3H, m, H-2',5',6'), 6.40 (2H, s, H-5,6), 4.62 (1H, d, J=7.5 Hz, H-2), 4.0 (1H, brs, OH-3), 4.0 (1H, m, H-3), 2.89 (1H, dd, J=5 and 15 Hz, H-4eq), 2.71 (1H, dd, J=8 and 15.0 Hz, H-4ax).

2. (−)-3',4',7,8-tetra-O-benzyl mesquitol (2): m.p 128° C., FABMS 651 ($M^+$+H), $^1$H NMR (200 MHz, $CDCL_3$) δ 7.48–7.16 (20H, m, H-4xO$CH_2$Ph), 7.02 (1H, s, H-2'), 6.92 (2H, s, H-5',6'), 6.68 (1H, d, J=8 Hz, H-5), 6.50 (1H, d, J=8 Hz, H-6), 5.15–5.01 (8H, each s, H-4xOC$H_2$Ph), 4.61 (1H, d, J=7.2 Hz, H-2), 3.90 (1H, m, H-3), 2.95 (1H, dd, J=5.2 and 15.5 Hz, H-4eq), 2.78 (1H, dd, J=7.5 and 15.5, H-4ax).

3. (−)-3-O-acetyl mesquitol (4a): m.p 78° C., FABMS 333 (M$^+$+H), $^1$H NMR (200 MHz, acetone-d$_6$) δ 6.85–6.65 (3H, m, H-2',5',6'), 6.44 (2H, s, H-5,6), 5.25 (1H, q, H-3), 5.08 (1H, d, J=5.8 Hz, H-2), 2.91 (1H, dd, J=5.2 and 16 Hz, H-4eq), 2.77 (1H, dd, J=6.3 and 16.5 Hz, H-4ax), 1.92 (3H, s, —CH$_3$).

4. (−)-3-O-butyryl mesquitol (4b): m.p 80° C., FABMS 383 (M$^+$+23), $^1$H NMR (200 MHz, acetone-d$_6$) δ 6.65–6.84 (3H, m, H-2',5',6'), 6.42 (2H, s, H-5,6), 5.25 (1H, q, H-3), 5.02 (1H, d, J=6.3 Hz, H-2), 3.02 (1H, dd, J=5.2 and 16.4 Hz, H-4eq), 2.82 (1H, dd, J=7 and 16.3 Hz, H-4ax), 2.15 (2H, t, H-2"), 1.46 (2H, m, H-3"), 0.78 (3H, t, H-4").

5. (−)-3-O-hexanoyl mesquitol (4c): m.p 81° C., FABMS 389 (M$^+$+H), $^1$H NMR (200 MHz, acetone-d$_6$) δ 6.84–6.65 (3H, m, H-2',5',6'), 6.42 (2H, s, H-5,6), 5.24 (1H, q, H-3), 5.02 (1H, d, J=6.5 Hz, H-2), 2.97 (1H, dd, J=5.2 and 16.4 Hz, H-4eq), 2.78 (1H, dd, J=7 and 16.3 Hz, H-4ax), 2.15 (2H, t, H-2"), 1.45 (6H, m, H-3"–5"), 0.78 (3H, t, H-6").

6. (−)-3-O-Decanoyl mesquitol (4d): m.p 84° C., FABMS 467 (M$^+$+23), $^1$H NMR (200 MHz, acetone-d$_6$) δ 6.85–6.65 (3H, m, H-2',5',6'), 6.45 (1H, d, J=8 Hz, H-5), 6.35 (1H, d, J=8 Hz, H-6), 5.23 (1H, q, H-3), 5.02 (1H, d, J=7.0 Hz, H-4), 2.95 (1H, dd, J=5.2 and 16.3 Hz, H-4eq), 2.75 (1H, dd, J=7 and 16.3 Hz, H-4), 2.15(2H, t, H-2"), 1.46 (2H, m, H-3"), 1.20 (12H, brs, H-4"–9"), 0.85 (3H, t, H-10").

7. (−)-3-O-myristoyl mesquitol (4e): m.p 83° C., FABMS 501 (M$^+$+H), $^1$H NMR (200 MHz, acetone-d$_6$) δ 6.85–6.65 (3H, m, H-2',5',6'), 6.45 (1H, d, J=8 Hz, H-5), 6.35 (1H, d, J=8 Hz, H-6) 5.23 (1H, q, H-3), 5.01 (1H, d, J=7.0 Hz, H-4), 2.95 (1H, dd, J=5.2 and 16.3 Hz, H-4eq), 2.75 (1H, dd, J=7 and 16.3 Hz, H-4), 2.16 (2H, t, H-2"), 1.45 (2H, m, H-3"), 1.20 (20H, brs, H-4"–13"), 0.85 (3H, t, H-14").

8. (−)-3-O-Palmitoyl mesquitol (4f): m.p 87° C., FABMS 529 (M$^+$+H), $^1$H NMR (200 MHz, acetone-d$_6$) δ 6.87–6.72 (3H, m, H-2',5',6'), 6.55 (1H, d, J=8 Hz, H-5), 6.45 (1H, d, J=8 Hz, H-6), 5.30 (1H, q, H-3), 5.02 (1H, d, J=7.5 Hz, H-2), 2.98 (1H, dd J=5.2 and 16.3 Hz, H-4eq), 2.80 (1H, dd, J=7 and 16.3 Hz, H-4ax), 2.18 (2H, t, H-2"), 1.45 (2H, m, H-3"), 1.25 (24H, brs, H-4"–15"), 0.89 (3H, t, H-16").

9. (−)-3-O-Steroyl mesquitol (4g): m.p 90° C., FABMS 557 (M$^+$+H), $^1$H NMR (200 MHz, acetone-d$_6$) δ 6.85–6.70 (3H, m, H-2',5',6'), 6.50 (1H, d, J=8 Hz, H-5), 6.40 (1H, d, J=8 Hz, H-6), 5.28 (1H, q, H-3), 5.01 (1H, d, J=7.5 Hz, H-2), 3.01 (1H, dd, J=5.2 and 16.3 Hz, H-4eq), 2.83 (1H, dd, J=7 and 16.3 Hz, H-4ax), 2.17 (2H, t, H-2"), 1.47 (2H, m, H-3"), 1.23 (28H, brs, H-4"–17"), 0.90 (3H, t, H-18").

10. (−)-3-O-benzoyl mesquitol (4h): m.p 248° C., FABMS 395 (M$^+$+H), $^1$H NMR (200 MHz, acetone-d$_6$) δ 7.92 (2H, m, H-2",6"), 7.60–7.46 (3H, m, H-3",4",5"), 6.95 (1H, brs, H-2'), 6.81 (2H, m, H-5',6'), 6.45 (2H, s, H-5,6), 5.50 (1H, q, H-3), 5.25 (1H, d, J=6.7 Hz, H-2), 3.10 (1H, dd, J=5.2 and 16.0 Hz, H-4eq), 2.95 (1H, dd, J=7.5 and 16 Hz, H-4ax).

11. (−)-3-O-(o-chloro benzoyl) mesquitol (4i): m.p 252° C., FABMS 429 (M$^+$+H), $^1$H NMR (200 MHz, acetone-d$_6$) δ 7.85 (1H, d, J=8 Hz, H-6"), 7.45 (1H, m, H-3"), 7.36 (2H, m, H-4",5"), 6.92 (1H, s, H-2'), 6.80 (2H, m, H-5',6'), 6.42 (1H, brs, H-5), 5.70 (1H, brs, H-6), 5.46 (1H, q, H-3), 5.21 (1H, d, J=7.2 Hz, H-2), 3.10 (1H, dd, J=6.0 and 16.2 Hz, H-4eq), 2.90 (1H, dd, J=8.0 and 16.2 Hz, H-4ax).

12. (−)-3-O-(p-methoxy benzoyl) mesquitol (4j): m.p 254° C., FABMS 425 (M$^+$+H), $^1$H NMR (200 MHz, acetone-d$_6$) δ 7.78 (2H, d, J=8 Hz, H-2",6"), 6.82 (2H, d, J=8 Hz, H-3",5"), 6.75 (3H, m, H-2',5',6'), 6.52 (1H, d, J=8 Hz, H-5) 6.42 (1H, J=8 Hz H-6), 5.45 (1H, q, H-3), 5.15 (1H, d, J=6.5 Hz, H-2), 3.80 (3H, s, —OMe), 3.05 (1H, dd, J=5.2 and 16.0 Hz, H-4eq), 2.85 (1H, dd, J=7.5 and 16.0 Hz, H-4ax).

13. (−)-3-O-(p-flouro benzoyl) mesquitol (4k): m.p 263° C., FABMS 413 (M$^+$+H), $^1$H NMR (200 MHz, acetone-d$_6$) δ 7.95 (2H, m, H-3",5"), 7.22 (2H, m, H-2",6"), 6.93 (1H, s, H-2'), 6.80 (2H, m, H-5',6'), 6.44 (2H, s, H-5,6), 5.48 (1H, q, H-3), 5.22 (1H, d, J=6.5 Hz, H-2), 3.15 (1H, dd, J=5.2 and 16.0 Hz, H-4eq), 2.96 (1H, dd, J=7.5 and 16.0 Hz, H-4ax).

BRIEF DESCRIPTION OF THE ACCOMPANIED DRAWINGS

The invention is illustrated by following accompanying drawings wherein:

FIG. 1 represent the structure of (−)-mesquitol.

Scheme-1: represents synthetic routes for preparing aliphatic esters (4a–g) and aromatic esters (4h–k) of (−)-mesquitol.

Table.1 is a representation depicting the α-glucosidase inhibitory activities (IC$_{50}$ values) of compounds (4a–k).

TABLE 1

| Compound | IC$_{50}$ (μM) |
|---|---|
| 1 | 82.32 |
| 4a | 46.31 |
| 4b | 46.18 |
| 4c | 49.34 |
| 4d | 13.46 |
| 4e | 12.56 |
| 4f | 9.56 |
| 4g | 54.45 |
| 4h | 77.76 |
| 4I | 43.26 |
| 4j | 67.26 |
| 4k | 32.82 |
| 1-deoxy nojirimycin | 50 |

The invention claimed is:

1. Mesquitol and its semi-synthetic 3-O-alkyl or aryl esters represented by the general formula (4)

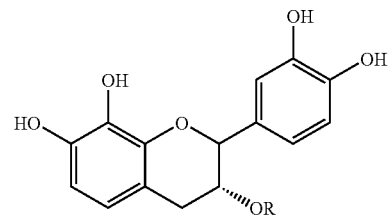

FORMULA (4)

wherein, R is selected from a group consisting of H, C$_n$H$_{2n+1}$ (n=1 to 16); and —COC$_6$H$_4$X, wherein X is selected from a group consisting of H, F, Cl, Br, I, NO$_2$, CN, NH$_2$, and OR$_1$ and R$_1$ is selected from a group consisting of H; and C$_n$H$_{2n+1}$ (n=1 to 8).

2. Compounds of claim 1, represented by general formula (4), where R is selected from the following table:

| Serial No. | Compound Code | R |
|---|---|---|
| 1. | 4a | Acetyl |
| 2. | 4b | Butyryl |
| 3. | 4c. | Hexanoyl |
| 4. | 4d. | Decanoyl |
| 5. | 4e | Myristoyl |
| 6. | 4f | Palmitoyl |
| 7. | 4g | Stearoyl |
| 8. | 4h | Benzoyl |
| 9. | 4i | o-chloro benzoyl |
| 10. | 4j | p-methoxy benzoyl |
| 11. | 4k | p-flouro benzoyl. |

3. Compounds of claim 1 have $IC_{50}$ value in the range of 32.0 to 83.0 μm.

4. A process for the preparation of semi-synthetic 3-O-alkyl or aryl esters of (−) mesquitol, the said process comprising steps of:
  a) drying the wood of Dichrostachys cinerea in shade,
  b) powdering the shade dried wood of step (a),
  c) extracting the powder of step (b) with petroleum ether, followed by halogenated hydrocarbon solvent to obtain the plant extracts and a plant residue,
  d) soaking the plant residue of step (c) in methanol, filtering and concentrating the methanol extract to obtain a residue,
  e) purifying the residue of step (d) over silica gel column by eluting with mixture of organic solvent,
  f) obtaining pure (−) mesquitol,
  g) adding to (−) mesquitol of step (f) anhydrous potassium carbonate, a ketonic solvent, benzyl halide and refluxed the mixture under nitrogen atmosphere for a time period of 2 hour to 8 hour,
  h) filtering the mixture of step (g), washing the residue with ketonic solvent, combining the filtrate and the wash, evaporating under reduced pressure to obtain a residue,
  i) purifying the residue of step (h) to obtain pure terra-O-benzyl-mesquitol of formula (2),
  j) treating the compound of formula (2) of step (i) with N,N'-Dicyclohexyl carbodiimide (DCC) required aliphatic acid in an anhydrous methylene chloride under nitrogen atmosphere followed by addition of 4-dimethyl aminopyridine, stirring the mixture for 6 h to 18 h at room temperature, filtering the mixture, washing the residue with methylene chloride, combining the filtrate and washing to obtain methylene chloride solution,
  k) washing the methylene chloride solution of step (j) with water, drying over anhydrous sodium sulphate, filtered, evaporating the solvent to obtain a residue,
  l) purifying the residue of step (k) to obtain the required 3-O-alkyl esters of tetra-o-benzyl (−) mesquitol of formulae 3a to 3g,
  m) providing a cooled solution of compound (2) in arihydrous methylene chloride along with triethyl amine, flushing nitrogen,
  n) adding required benzoyl chloride to step (in) mixture stirring the mixture for 2 h to 6 h at an ambient temperature,
  o) adding water to the reaction mixture of step (n), extracting with methylene chloride, separating methylee chloride layer and aqueous layer,
  p) drying methylene chloride layer of step (o) over anhydrous sodium sulphate, filtering and evaporating the solvent to obtain a residue,
  q) purifying the residue of step (p) to obtain 3-O-aryl ester of tetra-o-benzyl (−) mesquitol of formula 3h to 3k,
  r) stirring the compound of step (l) or step (q) in an alcoholic solution in the presence of palladium charcoal and hydrogen for a time period of 4 h to 8 h at room temperature, and
  s) filtering the mixture of step (r), removing the solvent from the filtrate to obtain the required 3-O-alkyl or aryl esters of (−) mesquitol of general formula (4).

5. A process of claim 4, wherein in step (e) the mixture of organic solvent used for eluting, is a mixture of chloroform and methanol.

6. A process of claim 4, wherein the mixture of solvent used is chloroform-methanol (96:4).

7. A process of claim 4, wherein the ketonic solvent used is selected from ethyl-methyl ketone, acetone or methyl isobutyl ketone.

8. A process of claim 7, wherein the ketonic solvent used is acetone.

9. A process of claim 4, wherein in step (j) the aliphatic acid used is selected from a group consisting of acetic acid, butyric acid, hexanoic acid, decanoic acid, myristic acid, palmitic acid or stearic acid.

10. A process of claim 4, wherein in step (n) the benzoyl chloride used is selected from a group consisting of halo benzoyl chloride, alkoxy benzoyl chloride, cyano benzoyl chloride, amino benzoyl chloride, or nitro benzoyl chloride.

11. A process of claim 10, wherein the halo benzoyl chloride used is o-chlorobenzoyl chloride or p-fluoro benzoyl chloride.

12. A process of claim 11, wherein the alkoxy benzoyl chloride used is p-methoxy benzyl chloride.

13. A process of claim 4,
  wherein palmitoyl, myristoyl and decanoyl esters of (−) mesquitol exhibit a higher α-glucosidase inhibitor activity than 1-deoxy nojirimycin and
  wherein the 3-O aromatic esters of (−) mesquitol are benzoyl, o-chlorobenzoyl, p-methoxy benzoyl or p-fluoro benzoyl esters.

14. A process of claim 4, wherein the 3-O-alkyl or aryl esters of (−) mesquitol obtained has $IC_{50}$ value in the range of 32.0 to 83.0 μm.

* * * * *